United States Patent
Brumbaugh

(10) Patent No.: US 6,235,300 B1
(45) Date of Patent: May 22, 2001

(54) PLANT PROTECTING ADJUVANT CONTAINING TOPPED OR PEAKED ALCOHOL ALKOXYLATES AND CONVENTIONAL ALCOHOL ALKOXYLATES

(75) Inventor: Ernest H. Brumbaugh, Rockford, MI (US)

(73) Assignee: Amway Corporation, Ada, MI (US)

(*) Notice: Subject to any disclaimer, the term of this patent is extended or adjusted under 35 U.S.C. 154(b) by 0 days.

(21) Appl. No.: 09/233,796

(22) Filed: Jan. 19, 1999

(51) Int. Cl.$^7$ .......................... A01N 25/00; A01N 63/00; A01N 31/14
(52) U.S. Cl. .......................... 424/405; 504/118; 504/161; 514/723
(58) Field of Search .................. 504/118, 161; 514/723; 424/405

(56) References Cited

U.S. PATENT DOCUMENTS

| | | | |
|---|---|---|---|
| 3,563,910 | 2/1971 | Fishman | 252/312 |
| 3,873,689 | 3/1975 | Frensch et al. | 424/78 |
| 3,951,888 | 4/1976 | Isayama et al. | 260/823 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,254,287 | 3/1981 | Ziegenhain et al. | 568/621 |
| 4,288,639 | 9/1981 | Camp | 568/625 |
| 4,302,613 | 11/1981 | Yang et al. | 568/618 |
| 4,306,093 | 12/1981 | Yang et al. | 568/618 |
| 4,456,697 | 6/1984 | Yang | 502/171 |
| 4,483,941 | 11/1984 | Yang | 502/171 |
| 4,540,828 | 9/1985 | Yang | 568/616 |
| 4,568,774 | 2/1986 | Yang et al. | 568/616 |
| 4,587,365 | 5/1986 | Anchor | 568/619 |
| 4,593,142 | 6/1986 | Yang | 568/618 |
| 4,681,617 | 7/1987 | Ghyczy et al. | 71/68 |
| 4,754,075 | 6/1988 | Knopf et al. | 568/618 |
| 4,775,653 | 10/1988 | Leach et al. | 502/170 |
| 4,793,850 | 12/1988 | Koester et al. | 71/79 |
| 4,840,942 | 6/1989 | Iwasaki et al. | 514/120 |
| 4,851,217 | 7/1989 | Mente | 424/83 |
| 4,922,029 | 5/1990 | Birnbach et al. | 568/616 |
| 4,966,728 | 10/1990 | Hazen | 252/354 |
| 4,983,323 | 1/1991 | Cox et al. | 252/551 |
| 4,983,389 | 1/1991 | Levy | 424/404 |
| 4,994,626 | 2/1991 | Greenough et al. | 568/618 |
| 5,075,058 | 12/1991 | Chan et al. | 264/118 |
| 5,078,782 | 1/1992 | Nielsen et al. | 71/100 |
| 5,084,087 | 1/1992 | Hazen et al. | 71/23 |
| 5,100,667 | 3/1992 | Chan et al. | 424/405 |
| 5,102,442 | 4/1992 | Hazen et al. | 71/91 |
| 5,118,650 | 6/1992 | King | 502/162 |
| 5,126,493 | 6/1992 | Hoelderich et al. | 568/616 |
| 5,130,413 | 7/1992 | Asai et al. | 528/408 |
| 5,152,823 | 10/1992 | Albrecht et al. | 71/79 |
| 5,160,528 | 11/1992 | Chaudhuri et al. | 71/79 |
| 5,178,795 | 1/1993 | Roberts | 252/356 |
| 5,180,587 | 1/1993 | Moore | 424/408 |
| 5,198,431 | 3/1993 | Röchling | 514/163 |
| 5,220,046 | 6/1993 | Leach et al. | 554/149 |
| 5,220,077 | 6/1993 | Sandolval et al. | 568/618 |
| 5,273,673 | 12/1993 | Ashrawi et al. | 252/70 |
| 5,273,953 | 12/1993 | Sżekely et al. | 504/116 |
| 5,290,751 | 3/1994 | Fiard et al. | 504/116 |
| 5,352,842 | 10/1994 | Weerasooriya et al. | 568/621 |
| 5,362,832 | 11/1994 | Cook | 562/333 |
| 5,386,045 | 1/1995 | Weerasooriya et al. | 554/149 |
| 5,386,968 | 2/1995 | Coffey et al. | 252/70 |
| 5,389,386 | * 2/1995 | Winston et al. | 424/717 |
| 5,393,791 | 2/1995 | Roberts | 514/762 |
| 5,409,885 | 4/1995 | Derian et al. | 504/116 |

FOREIGN PATENT DOCUMENTS

| | | |
|---|---|---|
| 9278605 | 10/1997 | (JP) . |
| WO 88/09122 | 12/1988 | (WO) . |
| WO 91/08666 | 6/1991 | (WO) . |
| WO 96/00705 | 1/1996 | (WO) . |
| WO 99/26472 | 6/1999 | (WO) . |

OTHER PUBLICATIONS

Article, Varying Surfactant Type Changes Quizalofop–P Herbicidal Activity, Jerry M. Green, Weed Technology 1997, vol. 11:298–302.
Article, Effect of Homolog Distribution on the Toxicity of Alcohol Ethoxylates, Garcia et al., JAOCS, vol. 73, No. 7 (1996).
Article, Surfactant Structure and Concentration Strongly Affect Rimsulfuron Activity, Green et al., Weed Technology 1993, vol. 7:633–640.
Article, Surfactant & Detergents—The Effect of "Peaking" the Ethylene Oxide Distribution on the Performance of Alcohol Ethoxylates and Ether Sulfates, Michael F. Cox, JAOCS, vol. 67, No. 9 (Sep. 1990).
Article, Effects of the Ethylene Oxide Distribution on Nonionic Surfactant Properties, K.W. Dillan, JAOCS, vol. 62, No. 7 (Jul. 1985).
Article, Surface Tension and Spreading as Indicators of Spray Adjuvant Efficacy, Brumbaugh et al., Amway Corporation, Ada, Michigan and Department of Crop and Soil Sciences, Michigan State University, East Lansing, Michigan.
Article, Extended Summaries SCI Pesticides Group Symposium Third International Symposium on Adjuvants for Agrochemicals, Coble, Harold, Pestic. Sci. 1993, 38, 247–282.
Shell, Neodol product Guide for Alcoholls, Ethoxylates, and ethoxysulfates, Science, 30–32, 1991.*

* cited by examiner

Primary Examiner—Jose G. Dees
Assistant Examiner—Alton Pryor
(74) Attorney, Agent, or Firm—Brinks Hofer Gilson & Lione; G. Peter Nichols

(57) ABSTRACT

An plant protecting composition comprising a biocide component and an adjuvant component wherein the adjuvant component includes at least one surfactant selected from the group consisting of topped alcohol alkoxylates and peaked alcohol alkoxylates and combinations thereof in combination with a conventional alcohol alkoxylate.

4 Claims, No Drawings

PLANT PROTECTING ADJUVANT CONTAINING TOPPED OR PEAKED ALCOHOL ALKOXYLATES AND CONVENTIONAL ALCOHOL ALKOXYLATES

BACKGROUND OF THE INVENTION

This invention relates to plant protecting compositions containing adjuvant compositions, and in particular, to adjuvant compositions that contain a topped or peaked alcohol ethoxylate or combinations thereof in combination with a conventional alcohol ethoxylate.

Adjuvants are commonly used in plant protecting compositions to facilitate biocidal action or to facilitate or modify characteristics of the biocidal formulations or spray solutions. In order to enhance or modify the chemical and/or physical characteristics of certain pesticides, adjuvants are added to form a mixture for spraying. Since spray application can be critical to the performance of the agricultural chemical, adjuvants are added to reduce application problems such as chemical stability, incompatibility, solubility, suspension, foaming, drift, evaporation, volatilization, phytotoxicity, surface tension, droplet size and coverage. They can, depending on their type, enhance wetting, translocation, spreading, sticking, emulsifying, dispersing and biological activity. Adjuvants include wetting agents, crop oil concentrates, spreaders, stickers, buffering agents, foaming and anti-foaming agents, dispersing agents and drift control agents. Over 200 EPA-registered pesticides have specific recommendations on their labels for adjuvant use. For example, they are recommended to enhance biological activity of the pesticide and to reduce, minimize or eliminate spray application problems as previously noted. There are several different types of adjuvants recommended. To achieve consistent and effective results, the user must first select the desired type of adjuvant and then the appropriate product within that specific type for use with a particular biocide and then use that product at recommended rates. Adjuvants can be added to the biocide formulation (commonly called "ready-to-dilute") or at the applicator stage when the pesticide formulation is diluted with water or a suitable carrier into a spray tank (commonly called "tank mix").

Nonionic surfactants have been used as activator adjuvants to facilitate biocide penetration wetting, spreading, dispersing, solubilizing, emulsifying and other surface modifying properties to bring about enhanced biocidal action. These surfactants have also been used as spray-modifier adjuvants to facilitate sticking or spreading of wettable biocidal powders or to modify the drift properties of the biocide. Examples of common nonionic surfactants used as spray adjuvants can be found in *Adjuvants for Herbicides* (Weed Science Society of America 1982), which is incorporated herein by reference.

A common nonionic surfactant used as an adjuvant is an alkyl aryl oxylate such as nonyl ethoxylate phenol, also known as nonoxynol-10. Although nonoxynol-10 is effective, suitable alternatives are continually being sought.

An acceptable alternative is a conventional aliphatic alcohol alkoxylate, commonly called an alcohol alkoxylate, such as alcohol ethoxylates. Alcohol ethoxylates or ethylene oxide adducts are nonionic surfactants having functional properties such as wetting, foaming, emulsifying, and dispersing abilities as well as solubilization and detergent abilities. While the use of alcohol ethoxylates alone as adjuvants has been satisfactory, there is an ongoing effort to make adjuvants with improved herbicidal performance.

Surprisingly, it has been found that the addition of an adjuvant composition containing topped or peaked alcohol alkoxylates, or combinations thereof in combination with conventional alcohol alkoxylates to certain post emergent biocidal mixtures increases the efficacy of these biocides beyond that of recognized standards.

SUMMARY OF THE INVENTION

The present invention relates to a plant protecting composition comprising an effective amount of agricultural biocide and from about 1% to about 40% of an adjuvant composition comprising a combination of nonionic surfactants selected from the group consisting of topped alcohol alkoxylates and peaked alcohol alkoxylates and combinations thereof with conventional alcohol alkoxylates. Preferably, the topped and peaked alcohol alkoxylates include alcohol ethoxylates, alcohol propoxylates, propoxylated and ethoxylated alcohols and combinations thereof. More preferably, the adjuvant composition includes primary aliphatic alcohol alkoxylates. The plant protecting composition may also contain other surfactants and additives so long as they do not detract from the improved results obtained from the adjuvant of the present invention.

The present invention further includes a method for increasing the efficacy of an agricultural biocide formulation comprising the step of providing an adjuvant comprising a nonionic surfactant selected from the group consisting of topped alcohol alkoxylates and peaked alcohol alkoxylates and combinations thereof with conventional alcohol alkoxylates. In one embodiment, the adjuvant composition and a biocide component are added to a tank mix. In another embodiment, the adjuvant is combined with the biocide component in a ready-to-dilute formulation.

Unexpectedly, it has been found that the adjuvant of the present invention improves the efficacy of certain post emergent agricultural biocide formulations beyond that of recognized standards.

It is noted that, unless otherwise stated, all percentages given in this specification and the appended claims refer to percentages by weight.

These and other advantages and features of the present invention will be better understood upon review of the following detailed description of the preferred embodiments.

DETAILED DESCRIPTION OF THE PREFERRED EMBODIMENTS

The present invention relates to a plant protecting composition containing an adjuvant composition comprising a nonionic surfactant component selected from the group consisting of topped alcohol ethoxylates and peaked alcohol ethoxylates and combinations thereof with conventional alcohol alkoxylates.

Alcohol alkoxylates useful in the present invention are those containing an aliphatic hydrocarbon chain and an polyoxyalkylene chain.

The hydrocarbon chain may be derived from an aliphatic alcohol. Examples of alcohol alkoxylates useful as nonionic surfactants usually include those containing a fatty alcohol chain having a carbon length of from about $C_8$ to about $C_{20}$. The oxyalkylene chain of the compound can have a length of from $C_2$ to about $C_{10}$. Alcohol alkoxylates useful as nonionic surfactants will preferably contain a oxyalkylene chain consisting mainly of ethylene oxide units (commonly called alcohol ethoxylates), propylene oxide units (commonly called alcohol propoxylates) or a combination thereof (commonly called propoxylated and ethoxylated alcohols).

Alcohol alkoxylates are generally prepared by alkoxylating the aliphatic alcohol with the oxyalkylene in the presence of a catalyst such as potassium oxide or sodium oxide. Examples of alcohol ethoxylates and alcohol propoxylates useful as nonionic surfactants include $C_8$–$C_{18}$ alcohols with 1–15 moles of ethylene oxide (EO) or propylene oxide (PO) units per mole of alcohol. The distribution of ethoxylation or propoxylation, as the case may be, is quite broad and a sizable amount of free alcohol is left in the product. Common conventional alcohol ethoxylates are listed under the chemical classification of "ethoxylated alcohols" in McCutcheon's *Emulsifiers & Detergents*, Annual 1992. Common conventional alcohol propoxylates as well as propoxylated and ethoxylated alcohols are listed under the chemical classification "propoxylated & ethoxylated fatty acids, alcohol or alkyl phenols" in McCutcheon's. The relevant portions of McCutcheon's are incorporated herein by reference.

Certain alcohol alkoxylates useful in the present invention are selected from the group consisting of topped alcohol alkoxylates, peaked alcohol alkoxylates and combinations thereof.

Topped alcohol alkoxylates refer to a distribution containing $C_6$ or higher carbon chain monofunctional and polyfunctional alcohols. Topped alcohol alkoxylates include both linear and branched alcohol alkoxylates. Topped alcohol alkoxylates have free alcohol and low mole alkoxylate entities removed physically by conventional separation processes such as extraction and distillation. Particularly preferred topped alcohol alkoxylates contain primary alcohol alkoxylates having $C_6$ or greater carbon chains.

Peaked alkoxylates refers to a narrow, high mole adduct distribution from the ethoxylation of linear or branched alcohols. Peaked alkoxylates have a more narrow and highly peaked alkoxylation distribution that results in a low amount of residual free alcohol, a lower amount of lower oxyalkylene adducts and a lower amount of higher oxyalkylene adducts in the product. Peaked alcohol alkoxylates are obtained through the use of different catalysts and/or manufacturing conditions. Examples of the preparation of peaked alcohol ethoxylates include U.S. Pat. No. 4,210,764 to Yang et al. and U.S. Pat. No. 5,118,650 to King, the disclosures of which are incorporated herein by reference.

The preferred peaked alcohol alkoxylates of the present invention include alcohol alkoxylates having a residual free alcohol content of less than about three percent. Particularly preferred peaked alcohol alkoxylates are $C_6$–$C_{20}$ alcohol ethoxylates, $C_6$–$C_{20}$ alcohol propoxylates, $C_6$–$C_{20}$ propoxylated and ethoxylated alcohols and combinations thereof.

The more preferred peaked alcohol alkoxylates are $C_8$–$C_{16}$ alcohol ethoxylates containing from about 2 to about 20 moles of ethylene oxide (EO) per molecule, $C_8$–$C_{16}$ alcohol propoxylates containing from about 2 to about 20 moles of propylene oxide (PO) per molecule, $C_8$–$C_{16}$ propoxylated and ethoxylated alcohols.

The more preferred topped and peaked alcohol alkoxylates are the biodegradable aliphatic alcohol alkoxylates, in particular primary aliphatic alcohol alkoxylates, and more preferably linear primary alcohol alkoxylates.

The adjuvant composition of the present invention may also contain other ingredients found in commercial adjuvants so long as they do not detract from the beneficial effects of the present invention. Examples of optional ingredients include additional surfactants, viscosity modifiers, stabilizing agents, pH modifiers, corrosion inhibitors, and the like. Examples of such optional ingredients can be found in U.S. Pat. No. 5,084,087 to Hazen et al., which is incorporated herein by reference.

The adjuvant composition of the present invention may be combined with one or more biocide components in various forms. For example, the adjuvant composition can be added to tank mixes with the biocide component(s). Alternatively, the adjuvant composition of the subject invention can be incorporated into a ready-to-dilute formulation containing the biocide component(s). Common forms of ready-to-dilute formulation include, for example, dispersible powders, non-dispersible powders, oil solubles, liquid concentrates or aqueous solutions.

The agricultural biocide component can be, for example, a fungicide, herbicide, insecticide, nematocide, acaricide and mixtures thereof. By "agricultural biocide" it is meant any biocide, pesticide, or herbicide. The type of the biocide component used is not critical to the use of the adjuvant composition according to the invention. Examples of common biocides are listed in U.S. Pat. No. 4,793,850 to Koester et al. and in U.S. Pat. No. 4,851,421 to Iwasaki et al., the entire disclosures of which are incorporated herein by reference.

The plant protection composition resulting from the combination of adjuvant and biocide component contains an effective amount of biocide component. The "effective amount" can be experimentally determined and depends upon the type and form of biocide used. For example, a ready-to-dilute plant protecting composition may include from about 1 to about 95% biocide, by weight of the composition. Ready-to-dilute formulations in the dry flowable powder form usually contains greater than about 90% biocide, while other powdered formulations can contain less than 30% biocide. In addition, ready-to-dilute formulations in the form of emulsifiable concentrates can contain up to about 40% biocide, while the concentration of biocide in suspension concentrates can be about 60%.

The adjuvant composition of the present invention can be added to a tank mix generally in amounts of from 0.0001 to about 10% of the tank mix. Preferably, the adjuvant composition is from 0.001% to about 5% by weight of the tank mix. More preferably, the adjuvant composition can be added to the tank mix in amounts of from 0.005% to about 2% by weight of the formulation. Most preferably, the adjuvant composition is from 0.01% to about 0.5% by weight of the formulation. In a preferred embodiment, the adjuvant 1.0 composition of the present invention has a Hydrophilic-Lipophilic Balance (HLB) that matches the HLB of the active biocide component. The adjuvant composition of the present invention can be added to the ready-to-dilute biocide formulation generally in amounts of from 1 to 40 percent of the tank mix so as to result in tank mix concentration specified above.

The adjuvant composition of the present invention can also be combined with the biocide component along with other ingredients such as other surfactants and adjuvants. Examples of these optional ingredients include, but are not limited to solvents, co-solvents, preservatives, corrosion inhibitors, thickening agents and buffering agents.

The advantages and other characteristics of the present inventions are best illustrated by the following examples.

EXAMPLES

In the examples, the performance of compositions containing commonly used surfactants were compared with those of compositions containing topped or peaked alcohol ethoxylates. Table I lists the chemical description of the various surfactants used.

TABLE I

| Surfactant | Chemical Description |
| --- | --- |
| Alfonic 610-50R | ethoxylated linear alcohols (50% EO) |
| Alfonic 810-60 | ethoxylated linear alcohols (60% EO) |
| Alfonic 1412-60 | ethoxylated linear alcohols (60% EO) |
| APSA-80 | ethoxylated nonyl phenol |
| Genapol UD 079 | $C_{11}$ linear alcohol ethoxylate containing an average of 7 moles EO/mole alcohol |
| Genapol 26 L 60 N | peaked $C_{12-16}$ linear primary alcohol containing an average of 7 moles EO |
| Genapol UD 070N | peaked $C_{11}$ linear alcohol ethoxylate containing an average of 7 moles EO |
| Genapol UD 080N | peaked $C_{11}$ linear alcohol ethoxylate containing an average of 8 moles EO |
| Neodol 1-7 | $C_{11}$ linear primary alcohol ethoxylate containing an average of 7 moles EO/mole alcohol |
| Neodol 23-6.5T | topped $C_{12}$-$C_{13}$ linear alcohol ethoxylate containing an average of 6.5 moles EO/mole alcohol |
| Neodol 23-9 | $C_{12}$-$C_{13}$ linear alcohol ethoxylate containing an average of 9 moles EO/mole alcohol |
| Neodol 91-6 | $C_9$-$C_{11}$ linear primary alcohol ethoxylate containing an average of 6 moles EO/mole alcohol |
| Nonoxynol 10 | ethoxylated nonyl phenol (10% EO) |
| Novel II 1412-70 | peaked $C_{12}$-$C_{14}$ linear primary alcohol ethoxylate (70% EO) |
| Novell II 1012-7 | peaked $C_{10-12}$ linear alcohol ethoxylate containing an average of 7 moles EO |
| Novel II 1012-5.5 | peaked $C_{10-12}$ linear alcohol ethoxylate containing an average of 5.5 moles EO |
| Silwet | silicon glycol copolymer |
| Toximul 8304 | alcohol ethoxylate blend containing an average of 6 moles EO/mole alcohol |
| Triton XL-80N | short-chain secondary alcohol alkoxylate blend containing ethylene oxide and propylene oxide |
| X-77 | commercial product based on Nonoxynol-10 |

Following is a list of adjuvants and their manufacturers from which they may be obtained. Alfonic 610-50R, Alfonic 810-60, Alfonic 1412-70, Novel II 1412-70, Novel II 1216CO-7, Novel II 1012-7, Novel II 1012-5.5 can be obtained from CondeaVista. Genapol UD 070, Genapol UD 070, Genapol UD 070N, Genapol 26-L-60N, and Genapol UD 080N can be obtained from Clariant Corporation. Neodol 1-7, Neodol 23-6.5T, Neodol 23-9, and Neodol 91-6 can be obtained from The Shell Chemical Company. Silwet can be obtained from Osi. Toximul 8304 can be obtained from Stepan Chemical Company. Triton XL-80N can be obtained from Union Carbide. Accent Pinnacle can be obtained from DuPont. Beacon can be obtained from Ciba. Roundup can be obtained from Monsanto. Pursuit can be obtained from American Cyanamid. Gramoxone Extra can be obtained from Zeneca.

EXAMPLE 1

Weed control evaluation was performed on sprayable herbicide formulations containing a series of alternate surfactants to replace Nonoxynol-10, the accepted industry standard.

The results of this greenhouse study are shown in Table II. Table II provides the weed control rating in percentage. As shown in Table II, Neodol 23-6.5T, a topped alcohol ethoxylate, out-performed Nonoxynol 10 on the BeaconJ and RoundupJ herbicide brands in Giant Foxtail and Seedling Johnsongrass. Moreover, Neodol 23-6.5T, the topped alcohol ethoxylate was the only alcohol ethoxylate that performed close to Nonoxynol-10.

The amount of herbicide used corresponding to the herbicides is Table II is shown in the immediately following chart.

| Chart of Herbicides | |
| --- | --- |
| Herbicide | Amount |
| Accent | 3.5 g a.i./ha at 25 gpa |
| Beacon | 2.0 g a.i./ha at 25 gpa on seedling Johnson grass and 14.8 g a.i./ha on giant foxtail |
| Roundup | 0.3 lb./acre at 25 gpa |
| Pursuit | 24.7 g a.i./ha at 25 gpa |
| Pinnacle | 1.9 g a.i./ha at 25 gpa |

In the above chart, "a.i." means "active ingredient, "ha" is the abbreviation for hectare, and "gpa" means "gallons per acre spray volume."

TABLE II

WEED CONTROL RATING (YEAR 1)

| Herbicide Weed Specie | ACCENT Giant Foxtail | ACCENT Seedling Johnsongrass | BEACON Giant Foxtail | BEACON Seedling Johnsongrass | ROUNDUP Giant Foxtail | PURSUIT Velvet leaf | PINNACLE Velvet leaf | Total Average Rating |
|---|---|---|---|---|---|---|---|---|
| Adjuvant (at 0.5%) | | | | | | | | |
| Nonoxynol 10 | 81 | 75 | 66 | 72 | 88 | 71 | 61 | 73.4 |
| NeodoL 23-6.5T | 76 | 66 | 71 | 78 | 98 | 43 | 50 | 68.9 |
| Neodol 91-6 | 74 | 74 | 53 | 69 | 79 | 39 | 41 | 61.3 |
| Neodol 1-7 | 71 | 68 | 65 | 64 | 79 | 36 | 42 | 60.7 |
| Genapol UD079 | 70 | 72 | 61 | 68 | 76 | 36 | 34 | 59.6 |
| Triton XL-80N | 74 | 73 | 44 | 73 | 79 | 34 | 39 | 59.4 |
| X-77 | 65 | 63 | 58 | 54 | 59 | 53 | 45 | 56.7 |
| Toximul 8304 | 68 | 55 | 36 | 50 | 83 | 34 | 34 | 51.4 |
| Alfonic 610-50R | 61 | 49 | 53 | 56 | 79 | 31 | 28 | 51.0 |
| Alfonic 810-60 | 63 | 43 | 29 | 59 | 73 | 38 | 33 | 48.3 |
| Coupled Ethoxylate | 63 | 34 | 33 | 51 | 64 | 29 | 29 | 43.2 |
| Herbicide Alone | 4 | 13 | 14 | 6 | 61 | 23 | 8 | 18.4 |
| No Treatment | 0 | 0 | 0 | 0 | 0 | 0 | 0 | 0 |

EXAMPLE 2

Weed control evaluation was performed on sprayable herbicide formulations containing a peaked alcohol ethoxylate (Novel 11 1412-70) and compared to formulations containing Nonoxynol-10.

Table III provides the weed control rating in percentage. In this test, herbicides containing the peaked alcohol ethoxylate out-performed those that contained Nonoxynol-10 in weed control experiments on five herbicides and four weed species.

The amount of herbicide used corresponding to the herbicides in Table III is shown in the immediately following chart.

Chart of Herbicides

| Herbicide | Amount |
|---|---|
| Accent | 3.5 g a.i./ha at 25 gpa |
| Beacon | 2.0 g a.i./ha at 25 gpa on seedling Johnson grass and 14.8 g a.i./ha on giant foxtail |
| Roundup | 0.3 lb./acre at 5 gpa on velvet leaf and lambs quarters, and 0.15 lb. a.i./A on foxtail and Johnson grass |
| Pursuit | 24.7 g a.i./ha at 25 gpa |
| Pinnacle | 1.9 g a.i./ha at 25 gpa |

In the above chart, "a.i." means "active ingredient," "ha" is the abbreviation for hectare, and "gpa" means "gallons per acre spray volume."

TABLE III

WEED CONTROL RATING (YEAR 2)

| Herbicide Weed Specie | Accent Giant Foxtail | Accent Seedling Johnson-grass | Beacon Giant Foxtail | Beacon Seedling Johnson-grass | Round-up Giant Foxtail | Roundup Seedling Johnson-grass | Pinnacle Velvet leaf | Pinnacle Common Lambs-quarters | Pursuit Velvet leaf | Pursuit Common Lambs-quarters | Round-up Velvet leaf | Roundup Common Lambs-quarters | Total Average Rating |
|---|---|---|---|---|---|---|---|---|---|---|---|---|---|
| Adjuvant (at 0.5%) | | | | | | | | | | | | | |
| Novel II 1412-70 | 63 | 70 | 62 | 66 | 95 | 85 | 60 | 78 | 76 | 61 | 88 | 89 | 74.4 |

TABLE III-continued

WEED CONTROL RATING (YEAR 2)

| Herbicide Weed Specie | Accent Giant Foxtail | Accent Seedling Johnson-grass | Beacon Giant Foxtail | Beacon Seedling Johnson-grass | Round-up Giant Foxtail | Roundup Seedling Johnson-grass | Pinnacle Velvet leaf | Pinnacle Common Lambs-quarters | Pursuit Velvet leaf | Pursuit Common Lambs-quarters | Round-up Velvet leaf | Roundup Common Lambs-quarters | Total Average Rating |
|---|---|---|---|---|---|---|---|---|---|---|---|---|---|
| Nonoxy-nol-10 | 71 | 71 | 66 | 65 | 88 | 64 | 56 | 76 | 64 | 55 | 68 | 88 | 69.3 |
| X-77 | 53 | 56 | 57 | 44 | 84 | 65 | 44 | 66 | 59 | 40 | 73 | 90 | 60.9 |
| Herbicide Alone | 5 | 4 | 4 | 4 | 88 | 60 | 13 | 13 | 23 | 10 | 73 | 81 | 31.4 |
| Untreated | 0 | 0 | 0 | 0 | 0 | 0 | 0 | 0 | 0 | 0 | 0 | 0 | 0 |

Table IV contains the weed control rating in percentage. It is surprising that several peaked linear alcohol ethoxylates outperformed non-peaked alcohol ethoxylate, X-77.

TABLE IV

| | Accent Velvet-leaf | Gt Foxtail | Lambs-quarters | Pursuit Velvet-leaf | Gt Foxtail | Lambs-quarters | Pinnacle Velvet-leaf | Lambs-quarters | Roundup Gt Foxtail | Lambs-quarters | Gramoxone Extra Lambs-quarters | Average |
|---|---|---|---|---|---|---|---|---|---|---|---|---|
| Novel II 1412-70 | 50 | 68 | 61 | 59 | 62 | 48 | 80 | 76 | 91 | 71 | 86 | 68.4 |
| Genapol 26-L-60N | 39 | 57 | 53 | 4 | 55 | 44 | 46 | 75 | 78 | 86 | 51 | 55.3 |
| Genapol UD 080N | 36 | 56 | 43 | 39 | 59 | 43 | 38 | 73 | 65 | 61 | 39 | 50.2 |
| X-77 | 40 | 47 | 51 | 41 | 48 | 43 | 39 | 69 | 46 | 70 | 53 | 49.7 |
| Genapol UD 707N | 19 | 49 | 46 | 41 | 56 | 46 | 39 | 74 | 58 | 68 | 38 | 48.5 |
| Novel II 1012-7 | 22 | 56 | 46 | 40 | 52 | 50 | 45 | 66 | 58 | 58 | 31 | 47.6 |
| Novel II 1012-5.5 | 25 | 47 | 43 | 39 | 48 | 43 | 40 | 74 | 49 | 60 | 31 | 45.6 |
| Herbicide Alone | 10 | 5 | 9 | 25 | 10 | 9 | 17 | 11 | 53 | 52 | 26 | 20.6 |
| No Treatment | 0 | 0 | 0 | 0 | 0 | 0 | 0 | 0 | 0 | 0 | 0 | 0 |

The amount of herbicide used corresponding to the herbicides in Table IV is shown in the immediately following chart. The surfactant comprised 0.25% of the spray volume.

Chart of Herbicides

| Herbicide | Amount |
|---|---|
| Accent | 0.03125 lbs/acre at 25 gpa on velvetleaf and lambsquarters and 0.003125 lbs/acre at 25 gpa on giant Foxtail |
| Gramoxone Extra | 0.156 lbs/acre at 25 gpa |
| Roundup | 0.25 lbs/acre at 5 gpa on lambsquarters and 0.1 lbs/acre on foxtail |
| Pursuit | 0.022 lbs/acre at 25 gpa |
| Pinnacle | 0.0016 lbs/acre at 25 gpa |

In the above chart, "a.i." means "active ingredient, "ha" is the abbreviation for hectare, and "gpa" means "gallons per acre spray volume."

In a total of 74 field trial runs in which a nonoxynol-10 based spray adjuvant was compared with a peaked alcohol ethoxylate formulation, there was no significantly different average weed control between the two formulations. The nonoxynol-10 formulation had a weed control rating of 81.5% compared to the peaked formulations weed control of 80.5%. Both formulations, the peaked and non peaked, gave weed control that was significantly better than the herbicide alone which had a weed control of 71.8 percent. It is surprising and one would generally expect that crop yield would follow weed control. The surprising result is that the peaked adjuvant formulation had a higher crop yield than the nonoxynol-10 or herbicide treatment alone. The peaked adjuvant formulation had a normalized yield of 106.9%. The nonoxynol-10 formulation gave a normalized yield of 105.3%, which is 1.6% less than the peaked adjuvant formulation. This result is surprising in that the peaked formulation gave comparable weed control to the nonoxynol-10 formulation and gave a higher crop yield over a broad range of crops and herbicides.

Thus, in a preferred embodiment of the present invention, the plant protecting composition comprises a biocide in combination with an adjuvant composition comprised essentially of a nonionic surfactant component selected from the group consisting of topped alcohol ethoxylates, peaked alcohol ethoxylates, topped alcohol propoxylates, peaked alcohol propoxylates, topped propoxylated and ethoxylated alcohols, peaked propoxylated and ethoxylated alcohols and combinations thereof and in combination with conventional alcohol alkoxylates, wherein the peaked surfactants contain less than about 3% residual free alcohol.

Additionally, the plant protecting composition may contain approximately 9% isopropanol, approximately 0.5% sodium benzoate, acetic acid, soft water and other components in addition to the peaked or topped alcohol alkoxylates and combinations thereof in combination with conventional alcohol alkoxylates.

A formulation of one preferred embodiment is shown in the Table V set forth immediately below.

TABLE V

FORMULATION

| Compound | Percentage |
|---|---|
| Toximul 8304 isodecyl Alcohol plus 6 moles of Ethylene Oxide conventional Alcohol Ethoxylate | 40 |
| Novell 11 1216 CO-7 $C_{12,14 \text{ and } 16}$ alcohol with 7 moles EO peaked alcohol ethoxylate | 40 |
| Isopropanol | 9 |
| Sodium Benzoate | 0.5 |
| Acetic Acid | as needed to obtain pH of 7 |
| Soft water | quantity sufficient |

Of course, it should be understood that a wide range of changes and modifications can be made to the embodiments described above. It is therefore intended that the foregoing description illustrates rather than limits this invention, and that it is the following claims, including all equivalents, which define this invention.

What is claimed is:

1. A plant protecting composition comprising an agricultural biocide and an adjuvant composition comprising a primary component selected from the group consisting of a peaked $C_{12}$–$C_{16}$ linear primary alcohol containing an average of 7 moles of ethylene oxide a peaked $C_{12}$–$C_{14}$ linear primary alcohol ethoxylate (70% ethylene oxide), and mixtures thereof.

2. The composition of claim 1 further comprising a topped alcohol alkoxylate having a $C_6$ or greater alkyl group.

3. A method for increasing the efficacy of an agricultural biocide formulation including a biocide component comprising providing an adjuvant composition selected from the group consisting of a peaked $C_{12}$–$C_{16}$ linear primary alcohol containing an average of 7 moles of ethylene oxide, a peaked $C_{12}$–$C_{14}$ linear primary alcohol ethoxylate (70% ethylene oxide), and mixtures thereof.

4. The method of claim 3 further comprising a topped alkoxylate having a $C_6$ or greater alkyl group.

* * * * *